(12) United States Patent
Hsieh et al.

(10) Patent No.: US 7,587,022 B1
(45) Date of Patent: Sep. 8, 2009

(54) CORRELATION-BASED MOTION ESTIMATION OF OBJECT TO BE IMAGED

(75) Inventors: Jiang Hsieh, Brookfield, WI (US); Yuchuan Wei, Iowa City, IA (US); Ge Wang, Iowa City, IA (US)

(73) Assignees: General Electric Company, Schenectady, NY (US); University of Iowa Research Foundation, Iowa City, IA (US)

( * ) Notice: Subject to any disclaimer, the term of this patent is extended or adjusted under 35 U.S.C. 154(b) by 167 days.

(21) Appl. No.: 11/277,243

(22) Filed: Mar. 23, 2006

(51) Int. Cl.
*A61B 6/00* (2006.01)
(52) U.S. Cl. .............................. 378/8; 378/4
(58) Field of Classification Search .............. 378/4–15, 378/95, 901
See application file for complete search history.

(56) References Cited

U.S. PATENT DOCUMENTS

| | | | | |
|---|---|---|---|---|
| 4,945,914 A * | 8/1990 | Allen | | 600/426 |
| 5,301,108 A | 4/1994 | Hsieh | | 378/8 |
| 5,602,891 A * | 2/1997 | Pearlman | | 378/62 |
| 5,673,300 A * | 9/1997 | Reckwerdt et al. | | 378/65 |
| 5,680,481 A * | 10/1997 | Prasad et al. | | 382/190 |
| 5,776,143 A * | 7/1998 | Adams | | 606/130 |
| 5,850,486 A * | 12/1998 | Maas et al. | | 382/294 |
| 6,249,568 B1 * | 6/2001 | Rizo et al. | | 378/98.12 |
| 6,373,920 B1 * | 4/2002 | Hsieh | | 378/98.11 |
| 6,385,286 B1 * | 5/2002 | Fitchard et al. | | 378/65 |
| 6,438,196 B1 * | 8/2002 | Cesmeli | | 378/8 |
| 6,496,560 B1 * | 12/2002 | Lin et al. | | 378/62 |
| 6,621,889 B1 * | 9/2003 | Mostafavi | | 378/65 |
| 6,661,873 B2 * | 12/2003 | Jabri et al. | | 378/98.11 |
| 6,745,066 B1 * | 6/2004 | Lin et al. | | 600/425 |
| 6,782,071 B1 * | 8/2004 | Tsuyuki | | 378/4 |
| 6,865,248 B1 * | 3/2005 | Rasche et al. | | 378/8 |
| 7,154,987 B2 * | 12/2006 | Rubin et al. | | 378/8 |
| 7,440,545 B2 * | 10/2008 | Kidani et al. | | 378/65 |
| 2002/0103428 A1 * | 8/2002 | deCharms | | 600/410 |
| 2002/0183610 A1 * | 12/2002 | Foley et al. | | 600/407 |
| 2003/0002616 A1 * | 1/2003 | Cesmeli | | 378/8 |
| 2003/0161436 A1 * | 8/2003 | Boyd et al. | | 378/8 |
| 2003/0235265 A1 * | 12/2003 | Clinthorne et al. | | 378/4 |
| 2005/0074084 A1 * | 4/2005 | Wang et al. | | 378/4 |
| 2005/0175144 A1 | 8/2005 | Hsieh | | 378/19 |
| 2005/0238135 A1 * | 10/2005 | Younis et al. | | 378/8 |

OTHER PUBLICATIONS

Michael Defrise et al., "A Combination of Rebinning and Exact Reconstruction Algorithms for Helical Cone-Beam CT,", (2001).

(Continued)

*Primary Examiner*—Edward J Glick
*Assistant Examiner*—Alexander H Taningco
(74) *Attorney, Agent, or Firm*—Ziolkowski Patent Solutions Group, SC

(57) ABSTRACT

An imaging system in an example comprises an x-ray source, a detector, a data acquisition system (DAS), and a computer. The x-ray source emits a beam of x-rays toward an object to be imaged. The detector receives x-rays emitted by the x-ray source. The DAS is operably connected to the detector. The computer is operably connected to the DAS and programmed to estimate motion of the object on a correlation-basis and through employment of earlier-collected data.

20 Claims, 14 Drawing Sheets

OTHER PUBLICATIONS

"Closed Curve" from MathWorld, (1999).
Eli Benveniste, "Comparison of Two-Dimensional Rebinning Algorithms for Image Reconstruction from Projections,", (1983).
Enrique Solano, "Concatenation and Rebinning of IUE High Resolution Spectra," pp. 1-8. Proceedings of the Conference held in Sevilla, Spain, Nov. 1997.
CT Rays vs. Image Reconstruction Journal of Visualization (2005).
CT Reconstruction Journal of Visualization (2005).
Michael Defrise et al., "Fourier Rebinning of Time-of-Flight PET Data," Phys. Med. Biol. 50 (2005) 2749-2763.
Yuchuan Wei et al., "General Formula for Fan-Beam Computed Tomography," PRL 95, 258102 (2005.
"Locus" from MathWorld (1888).
Yunnan Wu et al., "Smart Rebinning for the Compression of Concentric Mosaic," IEEE Transactions on Multimedia, vol. 4, No. 3, Sep. 2002.
"Tomographic Image Reconstruction," pp. 1-10. American Association of Physicists in Medicine (1999).

* cited by examiner

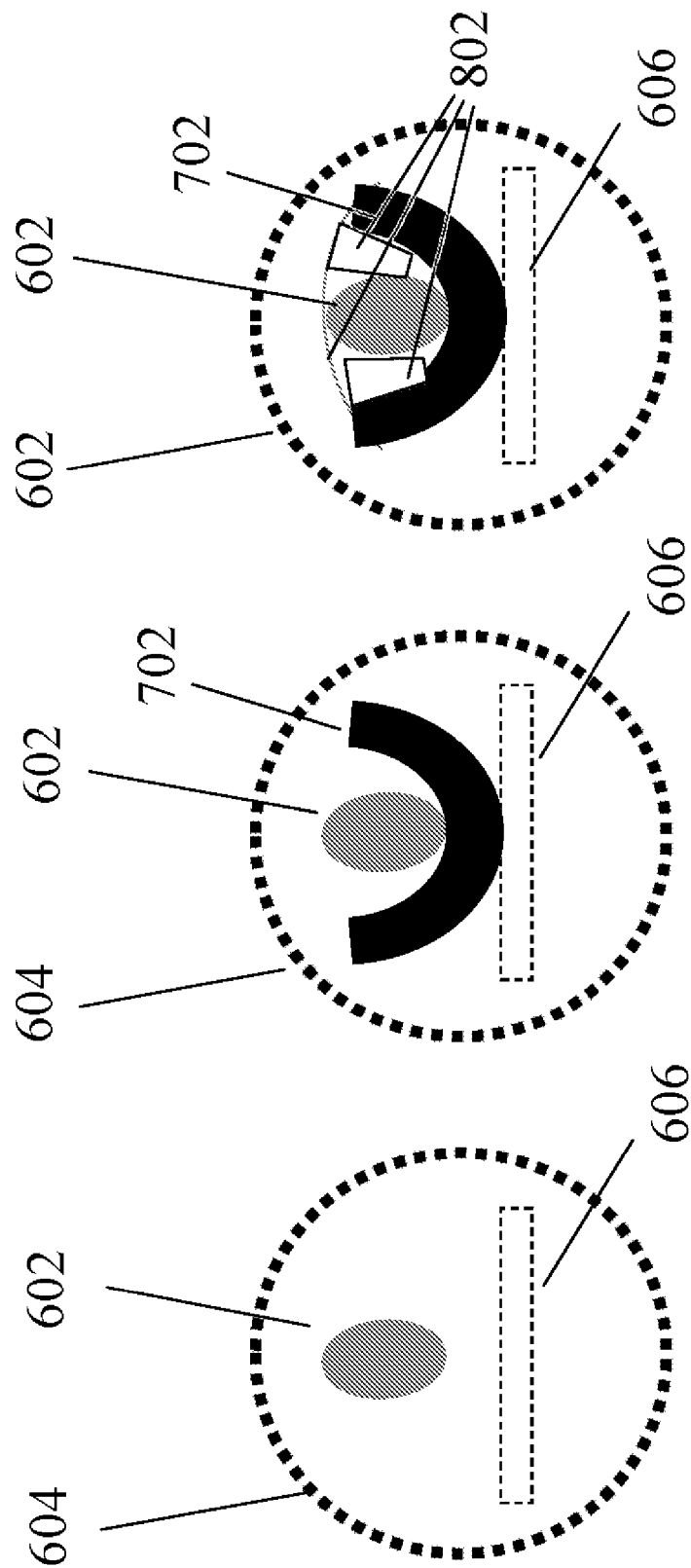

CORRELATION-BASED MOTION ESTIMATION OF OBJECT TO BE IMAGED

BACKGROUND OF THE INVENTION

The present invention relates generally to imaging and, more particularly, to motion estimation of an object to be imaged.

Exemplary imaging systems comprise computed tomography (CT) imaging systems and magnetic resonance (MR) systems. In a CT imaging system, exemplary geometries comprise fan-beam geometry and cone-beam geometry. Typically, in CT imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry opening within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

In head perfusion CT, the organ-of-interest is scanned in a cine mode (table remains stationary) while the contrast medium is injected into the patient and propagates in the blood circulation. From a sequence of reconstructed images, parameters such as the mean transit time (MTT), cerebral blood flow (CBF), and cerebral blood volume (CBV) can be calculated. These parameters can be used to differentiate viable versus nonviable tissues, and provide guidance to clinicians. To monitor the entire perfusion process, a patient is continuously scanned at a one second scan cycle for about fifty seconds. The rise and fall of the contrast medium is monitored within the blood vessels and all the other surrounding tissue. Based on the theses continuously scanned images, perfusion maps are calculated to show the distribution of several key physiological parameters for the brain.

A patient having a head CT may be unable to hold the head still and steady during the CT scanning. The movement of the head may result from the patient being young, old, severely injured, or other reasons. Head motion of the patient occurs more often in head perfusion CT. During the relatively long period of continuous scanning, head motion is often unavoidable and causes error in the generated perfusion map. Head motion in a perfusion study not only results in motion artifacts for individual images but also cause mis-registration of the group of images.

It is inconvenient for the patient to be asked to repeat the whole scanning process because of head motion during a short time. Therefore, it is desirable to develop a suitable approach so that the perfusion map can be formed even if the head motion exists.

BRIEF DESCRIPTION OF THE INVENTION

The invention in an implementation encompasses an imaging system. The imaging system comprises an x-ray source, a detector, a data acquisition system (DAS), and a computer. The x-ray source emits a beam of x-rays toward an object to be imaged. The detector receives x-rays emitted by the x-ray source. The DAS is operably connected to the detector. The computer is operably connected to the DAS and programmed to estimate motion of the object on a correlation-basis and through employment of earlier-collected data.

Another implementation of the invention encompasses a medical computed tomography (CT) system. The medical CT system comprises an x-ray source, a detector, a data acquisition system (DAS), and a computer. The x-ray source emits a beam of x-rays toward a head to be imaged. The detector receives x-rays emitted by the x-ray source. The DAS is operably connected to the detector. The computer is operably connected to the DAS and programmed to estimate the motion of the head during head perfusion based on correlation of data collected earlier during the head perfusion.

A further implementation of the invention encompasses a method. A beam of x-rays is emitted toward an object to be imaged. Motion of the object is estimated on a correlation-basis and through employment of earlier-collected data.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings:

FIG. 6 illustrates exemplary large head motion.

FIG. 7 illustrates exemplary moderate head motion.

FIG. 8 illustrates exemplary small head motion.

DETAILED DESCRIPTION OF THE PREFERRED EMBODIMENT

The operating environment of the present invention is described with respect to a four-slice computed tomography (CT) system. However, it will be appreciated by those skilled in the art that the present invention is equally applicable for use with single-slice or other multi-slice configurations. Moreover, the present invention will be described with respect to the detection and conversion of x-rays. However, one skilled in the art will further appreciate that the present invention is equally applicable for the detection and conversion of other high frequency electromagnetic energy. The present invention will be described with respect to a "third generation" CT scanner, but is equally applicable with other CT systems. Exemplary implementations comprise one or more of a "third generation" CT scanner, "fourth generation" CT scanner, and/or other type of CT system. The present invention is applicable to fan-beam, cone-beam, and/or other geometries. The present invention is further applicable to magnetic resonance (MR) systems and/or other modalities.

Figure 1:
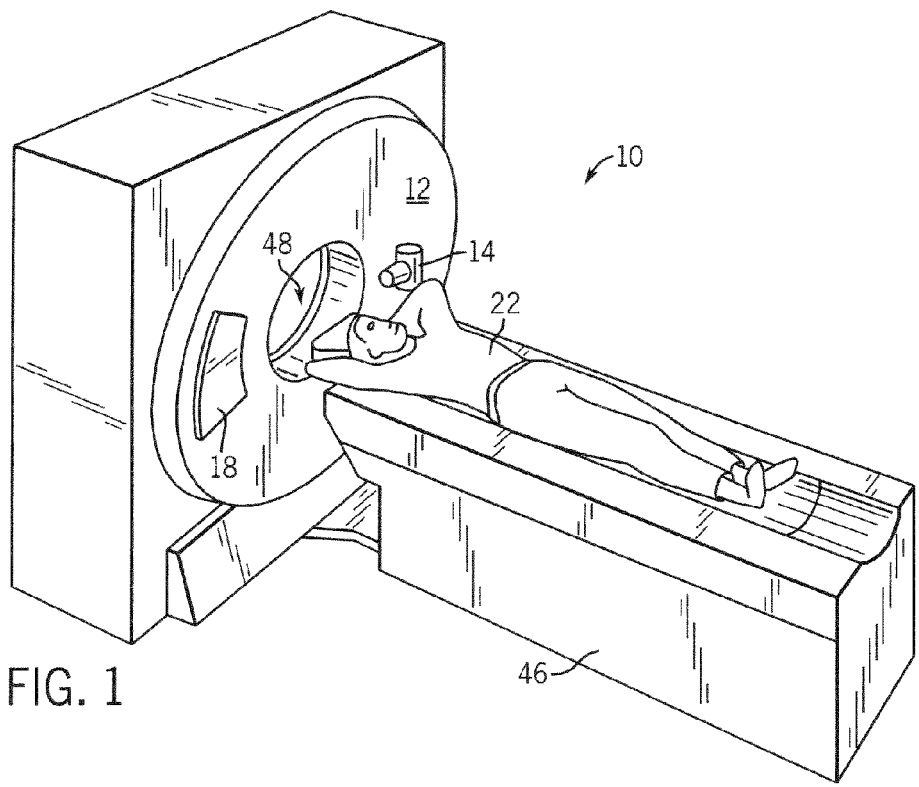
FIG. 1 is a pictorial view of a CT imaging system.
Figure 2:
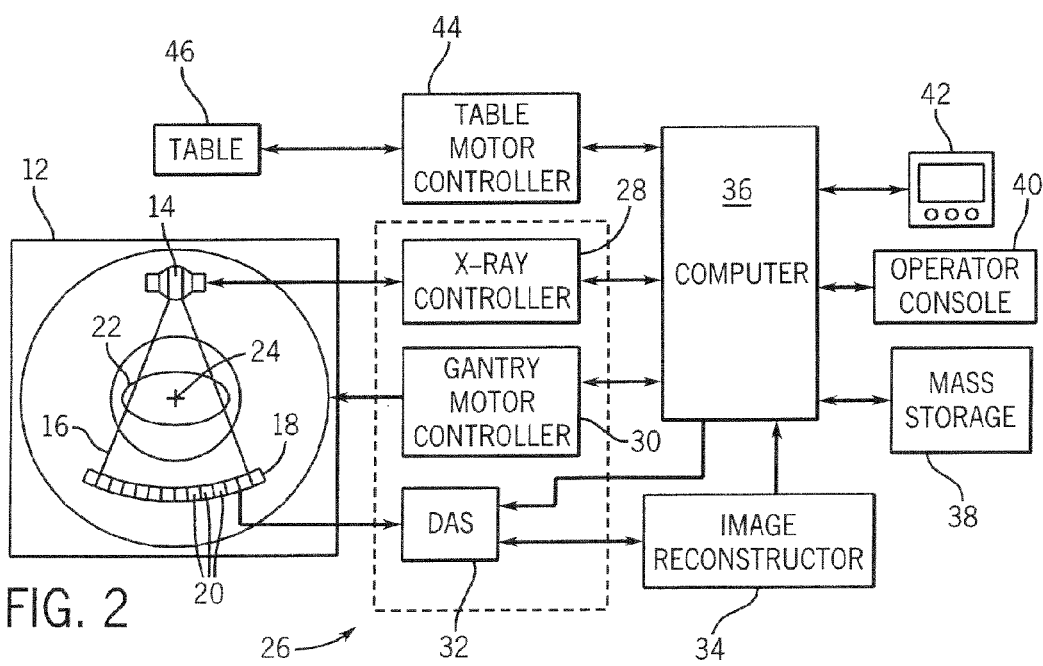
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from the DAS 32 and performs high speed reconstruction. The image reconstructor 34 in an example comprises a computer that interprets information from the DAS 32 and performs reconstruction of an object to be imaged. The image reconstructor 34 comprises a recordable data storage medium. The reconstructed image is applied as an input to a computer 36 which stores the image in a mass storage device 38. The mass storage device 38 comprises a recordable data storage medium, as described herein.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

Head perfusion CT in an example provides physiological parameter maps based on a sequence of reconstructed images when the contrast material passes through the brain. During an about fifty second scanning period, head motion is often unavoidable. Head motion has a potential to undesirably result in motion artifacts for individual images and/or cause mis-registration of the group of images. In an example, if the head motion is known, one can reconstruct the images using a noncircular reconstruction formula in the head system, for example, to avoid repeating the whole process of perfusion scan.

Figure 3:
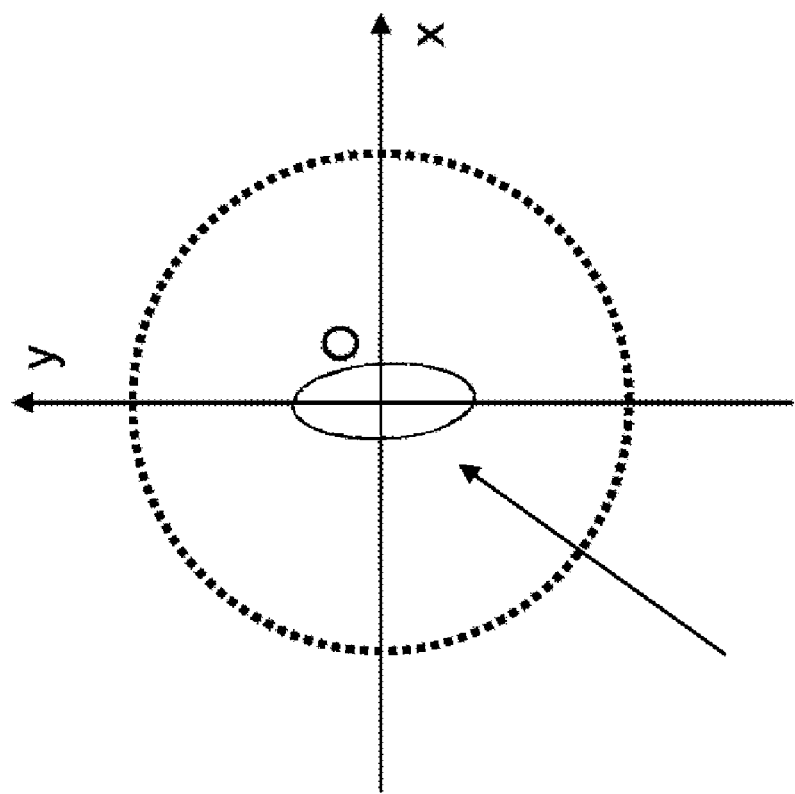
FIG. 3 represents an exemplary head perfusion case without head motion.

FIG. 3 represents an exemplary head perfusion case without head motion. In exemplary head perfusion CT, the head of the patient 22 is scanned in a cine mode (table remains stationary) while the contrast medium is injected into the patient 22 and propagates in the blood circulation. From a sequence of reconstructed images, parameters such as the mean transit time (MTT), cerebral blood flow (CBF), and cerebral blood volume (CBV) can be calculated. These parameters can be used to differentiate viable versus nonviable tissues, and provide guidance to clinicians. To monitor the entire perfusion process, the patient 22 in an example is continuously scanned at a one second scan cycle for about fifty seconds. The rise and fall of the contrast medium is monitored within the blood vessels and all the other surrounding tissue. Based on the continuously scanned images, perfusion maps are calculated to show the distribution of several key physiological parameters in the brain.

The patient 22 having a head CT in an example may be unable to hold the head still and steady during the CT scanning. The movement of the head may result from the patient 22 being young, old, severely injured, or other reasons. Head motion of the patient 22 occurs more often in head perfusion CT. During the relatively long period of continuous scanning, head motion is often unavoidable and causes error in the generated perfusion map.

Figure 4:
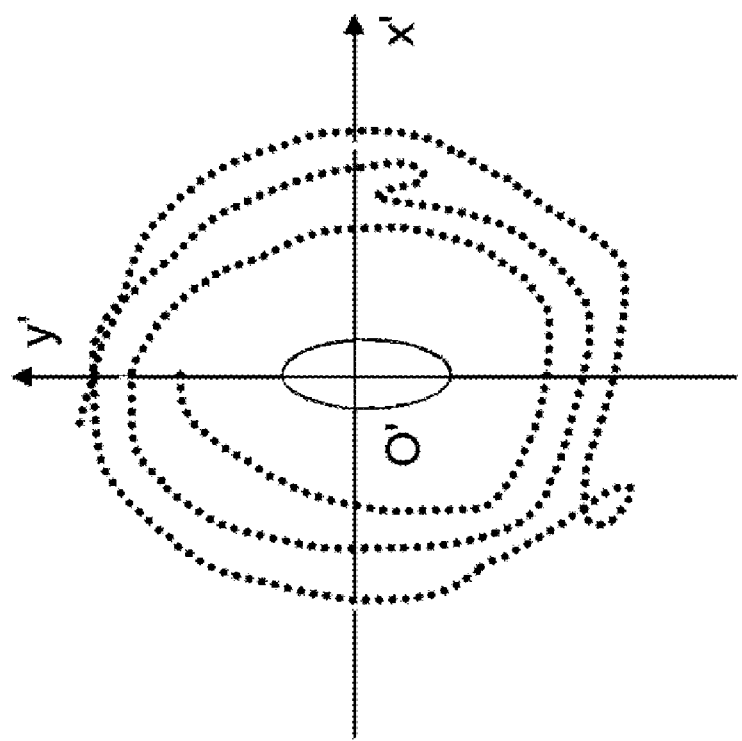
FIG. 4 represents an exemplary head perfusion case with head motion.

FIG. 4 represents an exemplary head perfusion case with head motion. During an exemplary head perfusion study, the head is moves from the original position O to the new position O'. The general motion of the head is described by (x(t), y(t), α(t)). Exemplary estimation of the motion is described herein.

Figure 5:
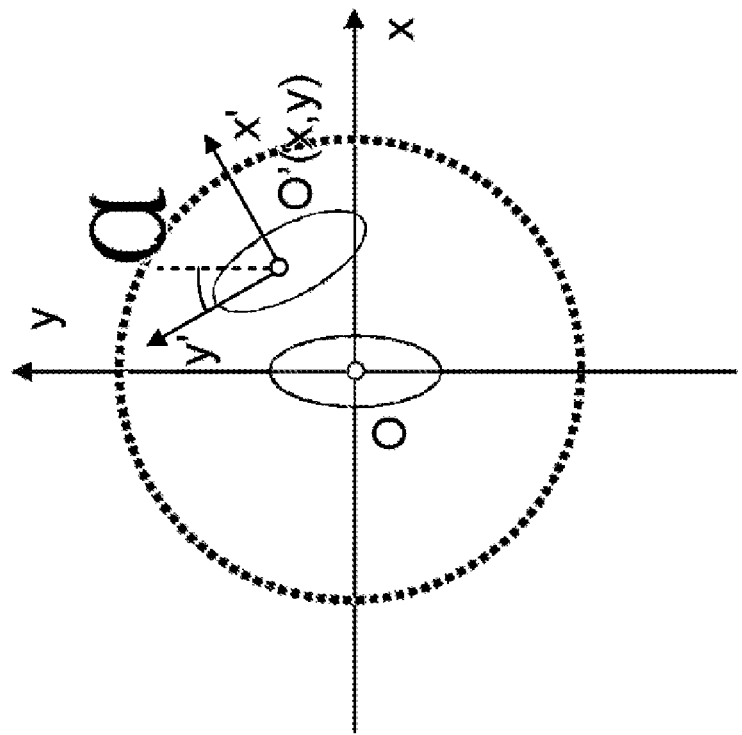
FIG. 5 illustrates exemplary equivalent motion of the source in an exemplary head system.

The head motion in an exemplary perfusion study not only results in motion artifacts for individual images but also causes mis-registration of the group of images. Elimination of the damage to images by head motion is desirable. FIG. 5 illustrates exemplary equivalent motion of the source in an exemplary head system. If the head motion is known, one can find the equivalent motion of the source and reconstruct the images in the head system O'X'Y' by a formula for general locus.

In an example, if the head motion of the patient 22 is known, one can find an equivalent motion of the x-ray source 14 and reconstruct the images in a system oriented with respect to the head of the patient 22. Estimation of the head motion is desirable. An exemplary basis for motion estimation comprises existence of a reference scan among other scans, for example, other scans in a scanning period such as a fifty second scanning period. In an example, the reference scan comprises substantially little and/or substantially no head motion and is used as a reference scan for other scans, for example, as a perfect reference scan. In a further example, the reference scan comprises no head motion at all and is used as a reference scan for other scans. A further exemplary basis for motion estimation comprises an exemplary assumption that the head motion comprises a rigid motion inside the scanning plane. For example, the reference scan comprises a good scan of the object.

For example, all the scans may contain some motion. One may pick a scan that comprises the least motion as the reference scan. The reference scan in an example is not free of any motion, but is the best of all other scan. In another example, multiple scans may be free of motion relative to the reference scan, but the patient has moved between the scans and the positions are different. One may pick a scan that is closest to the average position as the reference scan. In a further example, the reference scan comprises a good scan is a scan that is free of any motion.

An exemplary implementation estimates various head motion based on existing reference scans, for example, so that head perfusion images can be reconstructed with fewer artifacts and/or mis-registration when some head motions exist. Presented herein is an exemplary development of associated motion estimation approaches for large motion, moderate motion, and small motion. In an example, one may develop approaches for estimation of the various head motions as large motion, moderate motion, and small motion. For explanatory purposes, presented herein is an illustrative description based on exemplary assumptions that a) a reference scan exists among fifty scans in a scanning period such that the reference scan comprises no head motion at all and serves as a perfect reference scan for other scans, and that b) the head motion is a rigid motion inside the scanning plane.

FIG. 6 illustrates exemplary large head motion. Large motion in an example means the head 602 of the patient 22 can move in any position in the field of view (FOV) 604. For example, this may occur when the head holder 702 (FIG. 7) is not employed. Exemplary large motion estimation reconstructs the reference scan to obtain an object. Since the object is known, for every projection in a bad scan, one can find the actual position of the object by minimizing the error between a simulated projection and the measured projection. Position 606 comprises an exemplary position of the CT bed which in fact does not appear in the FOV 604 during the head perfusion.

FIG. 7 illustrates exemplary moderate head motion. For example, similar projections may be employed for motion estimation. Moderate motion in an example means the head 602 moves inside the head holder 702. For example, this may occur when the head holder 702 is used and other fixed material 802 (FIG. 8) is not employed. Exemplary moderate motion estimation sets up an approximate similar relation between the projections of the bad scan and reference scan. For every projection in a bad scan in an example one can find a projection in a reference scan so that they have similar profiles. Based on this, one may estimate motion parameters for reconstructions.

FIG. 8 illustrates exemplary small head motion. For example, rebinning may be employed for motion estimation. Small motion in an example means the motions of the head 602 with the head holder 702. For example, this may occur when the head 602 is fixed well but the head 602 has a minor unconscious motion. Such a small motion in an example does not produce motion artifacts but result in mis-registration of the images. For small motion estimation in an example one rebins the fan-beam projection to parallel beam projection. An exemplary position difference between the bad scan and reference scan can be found from the two rebinned projections of the bad scan and the reference scan, and target reconstruction can be used.

Additional exemplary details are presented herein in connection with the exemplary estimation approaches.

Exemplary details for exemplary large motion estimation are presented herein. With a reference scan, one can obtain clear reconstructed images of the head 602. For a known object and a measured projection, one can find an estimated optimal position by minimizing the error between the measured projection and simulated projection at an estimated position.

Figure 9:
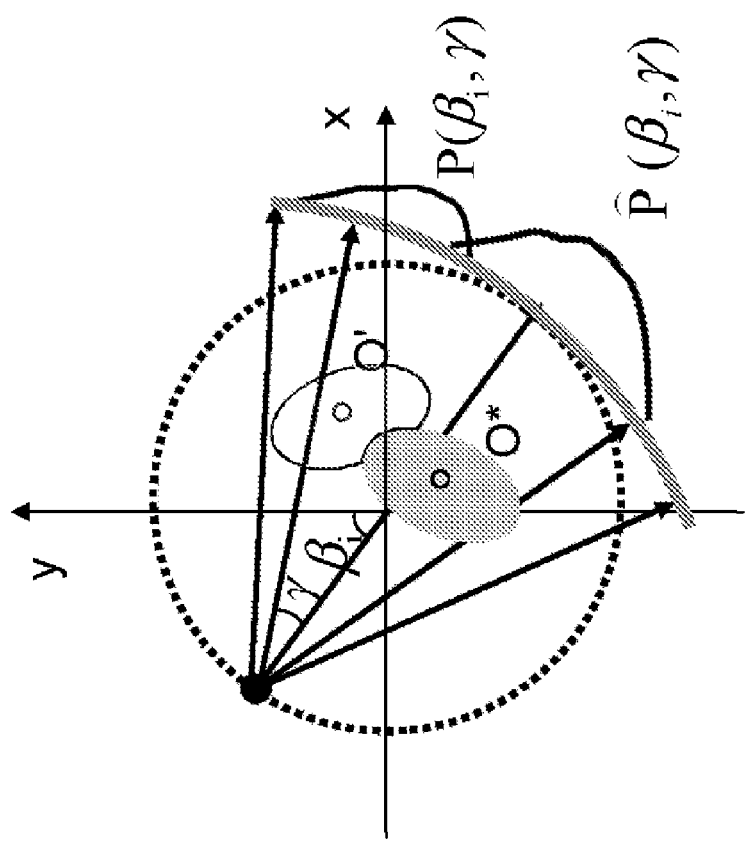
FIG. 9 illustrates a measured projection and an exemplary simulated projection.

FIG. 9 illustrates a measured projection and an exemplary simulated projection. One may in an example denote the measured projection in a bad scan by $P(\beta_i,\gamma)$ and the real position O' of the head 602 by $(x_i,y_i,\alpha_i)$, where the subscript $i=1,2,\ldots,N$ is the view index. Suppose the estimated position O* is $(\hat{x}_i,\hat{y}_i,\hat{\alpha}_i)$, and the simulated projection $\hat{P}(\beta_i,\gamma)$ can be generated by computer because one knows the object. One may define an exemplary object function by exemplary equation (1):

$$F(\hat{x}_i,\hat{y}_i,\hat{\alpha}_i)=\int_{-\gamma_m}^{\gamma_m}[\hat{P}_{\hat{x}_i,\hat{y}_i,\hat{\alpha}_i}(\beta_i,\gamma)-P(\beta_i,\gamma)]^2 d\gamma. \quad (1)$$

Through exemplary optimization of the object function one can obtain exemplary satisfactory estimated motion $(\hat{x},\hat{y},\hat{\alpha})$. With this estimated motion, one can reconstruct the image with a reconstruction formula for a general locus. One may use Shepp-Logan phantom to verify this approach. Suppose the radius of FOV is 1, and the radius of the X ray source locus is 4. The motion of the head is given as exemplary equations (2):

$$x = -0.25\sin\left(\frac{t}{T}\pi\right) \quad (2)$$
$$y = -0.25\cos\left(\frac{t}{T}2\pi\right)$$
$$\alpha = -90° \sin\left(\frac{t}{T}\pi\right).$$

With these parameters this motion can be considered as a large motion. T is the scan period, with a typical value of one second.

Figure 10:
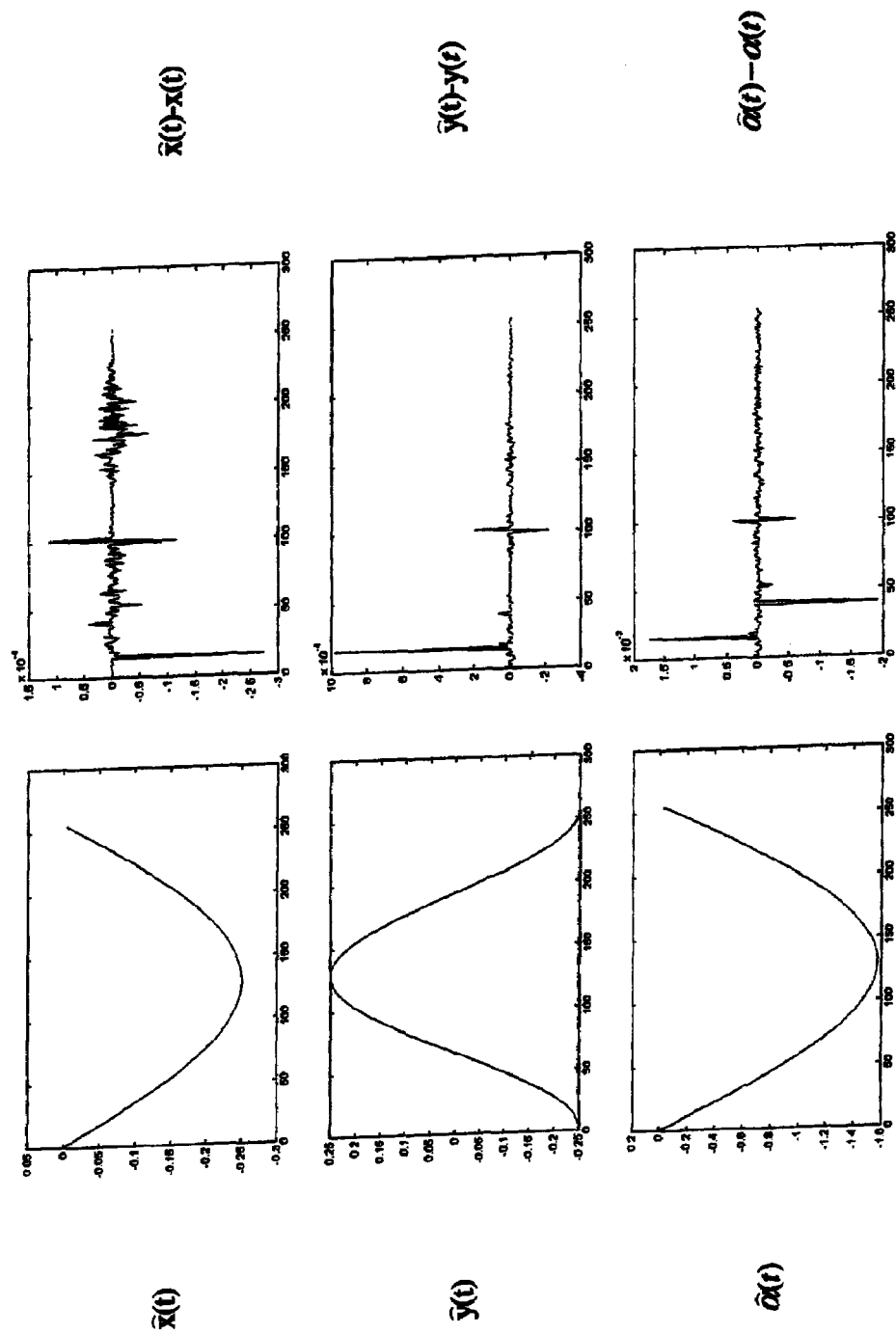
FIG. 10 illustrates exemplary estimated motion parameter and error: $(\hat{x}_i, \hat{y}_i, \hat{a}_i)$.

With the given motion and the phantom parameters, one may generate the projection data $P(\beta_i,\gamma)$ at 256 discrete time value $t_i=i/T$, $i=0, 1, \ldots, 255$. With this projection data, one may estimate the motion by the optimization method. One may employ an optimization approach called downhill simplex method with an associated command in Matlab of fminsearch. FIG. 10 illustrates exemplary estimated motion parameter and error. Exemplary estimated motion is denoted by $(\hat{x},\hat{y},\hat{\alpha})$. Exemplary errors are defined by exemplary equation (3):

error of $x=\hat{x}-x$, error of $y=\hat{y}-y$, error of $z=\hat{z}-z$. (3)

From the error shown in FIG. 10, one may see that the estimated value is accurately close to the true value.

Figures 11, 12:
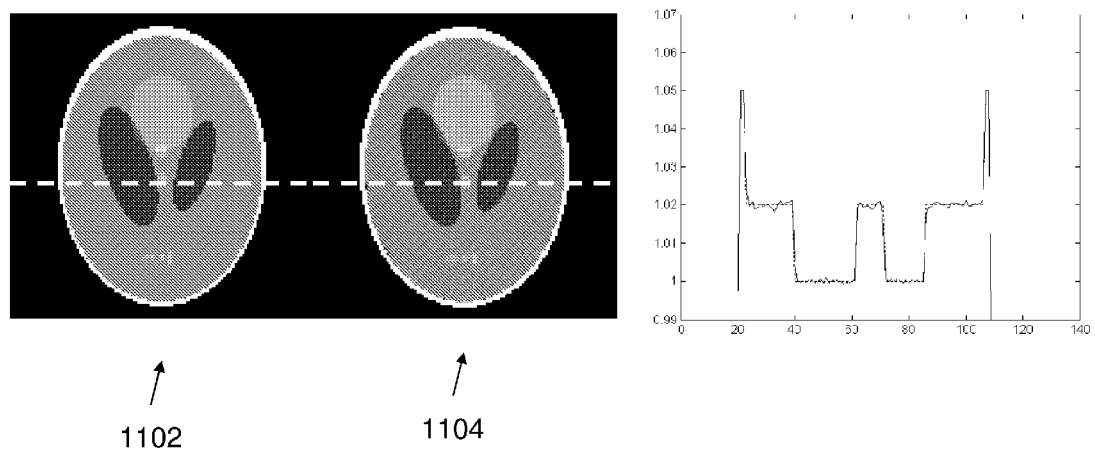
FIG. 11 illustrates exemplary phantom and reconstructed images from exemplary estimated motion information.
FIG. 12 illustrates exemplary profiles of the midline of the exemplary phantom and reconstructed images of FIG. 11.

FIG. 11 illustrates exemplary phantom image 1102 and exemplary reconstructed image 1104 from exemplary estimated motion information. The exemplary parameters used were $D_0=2$, the number of views 256, and the number of detectors 1024 which in an example are uniformly distributed along a half circle. The image size was set to 1*1 and discretized into a matrix of 128*128 pixels. The display window was set to [0.99, 1.05]. The relative error is 0.27%, which in an example is defined by exemplary equation (3). FIG. 12 illustrates exemplary profiles of the midline of the exemplary phantom image 1102 and the exemplary reconstructed image 1104. With the estimated motion, one can calculate the equivalent source motion and reconstruct the image by a non-circular locus reconstruction formula in the head system. See FIG. 5.

Exemplary details for exemplary moderate motion estimation are presented herein. Exemplary estimated moderate motion may be based on an exemplary approximate similar relation between the profiles of the bad scan and reference scan. An exemplary correlation coefficient may play a significant role. An exemplary assumption is that in a reference scan the center of the object is located at the origin of the system. One may consider a similar shape of projection profile at different location. An exemplary description is presented herein of an exemplary similar relation between projections of the same object at different locations.

Figure 13:
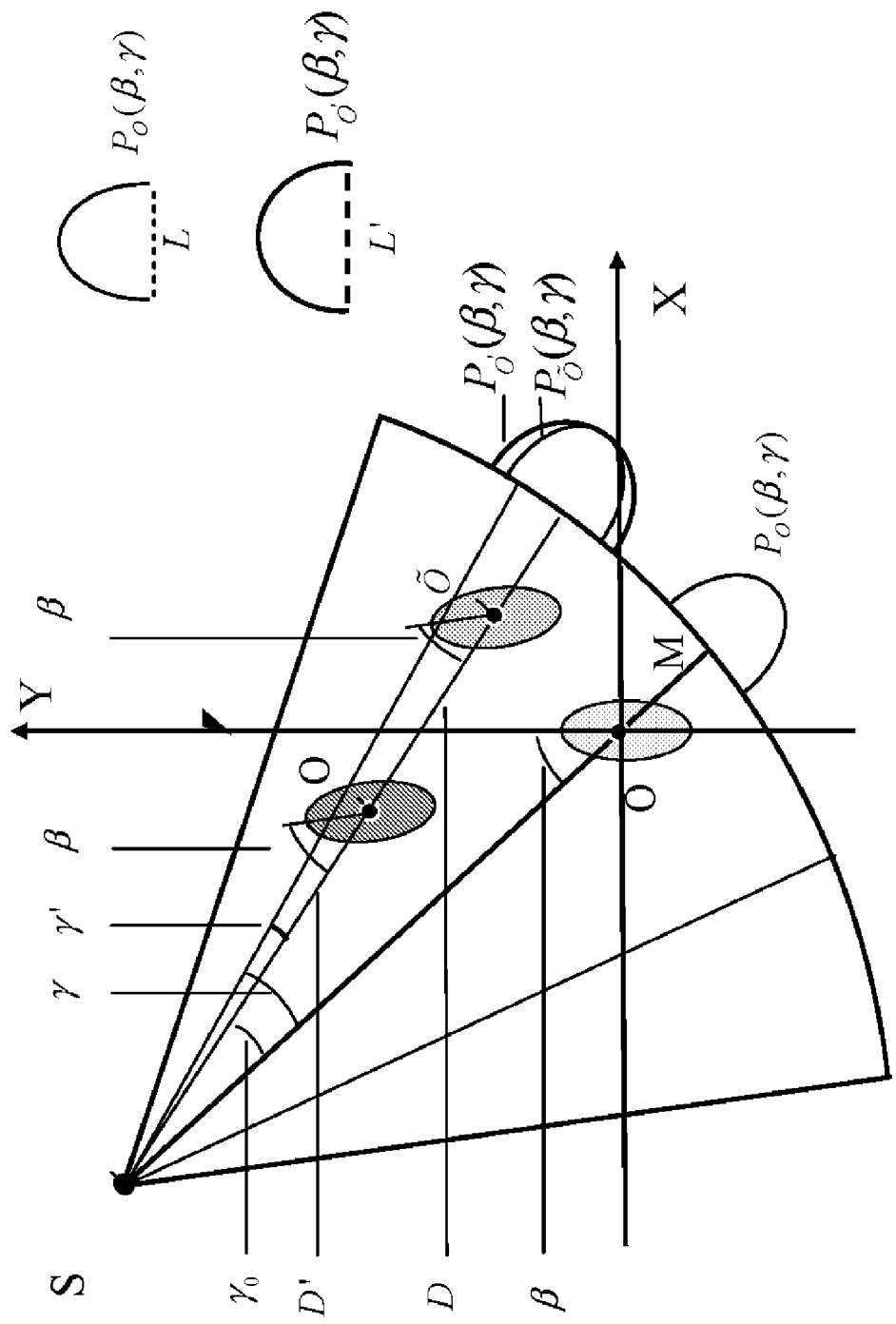
FIG. 13 illustrates an exemplary approximate similar relation of a same object at exemplary different locations.

FIG. 13 illustrates an exemplary approximate similar relation of a same object at exemplary different locations. In the XOY system, the source is located at the view angle β. The object gravity center now is located at the origin O. The projection of the object is denoted as $P_O(\beta,\gamma)$. Now suppose that the object is rotated an angle $\gamma_0$ along the S point counterclockwise to $\tilde{O}$ and then is translated along the x ray $S\tilde{O}$ to the final position O'. The associated projection is denoted as $P_{\tilde{O}}(\beta,\gamma)$ and $P_{O'}(\beta,\gamma)$. One may denote $SO=S\tilde{O}=D, SO'=D'$.

An exemplary relation between $P_O(\beta,\gamma)$, and $P_{\tilde{O}}(\beta,\gamma)$ is provided in exemplary equation (4):

$$P_O(\beta,\gamma-\gamma_0)=P_{\tilde{O}}(\beta,\gamma) \quad (4)$$

Due to the different distances from the source in an example the relation between $P_{\tilde{O}}(\beta,\gamma)$ and $P_{O'}(\beta,\gamma)$ can be approximately expressed in exemplary equation (5):

$$P_{\tilde{O}}(\beta,\gamma) \approx P_{O'}\left(\beta, \gamma_0 + (\gamma-\gamma_0)\frac{D}{D'}\right) \quad (5)$$

An exemplary condition for this approximate relation is that D' is near D.

Therefore, an exemplary final relation between $P_O(\beta,\gamma)$ and $P_{O'}(\beta,\gamma)$ is provided by exemplary equation (6):

$$P_O(\beta,\gamma-\gamma_0) \approx P_{O'}\left(\beta, \gamma_0 + (\gamma-\gamma_0)\frac{D}{D'}\right) \quad (6)$$

That is, the projections of the object in an example have a similar shape of profile when the object rotates along the source position and translates along the x-ray. For example, if the angle between the object and the x-ray passing through the gravity center does not change, the projections substantially consistently and/or always approximately have a similar shape. An exemplary relation is provided in exemplary equations (7) and (8):

$$\gamma_0 = \frac{\int_{-\gamma_m}^{\gamma_m} \gamma P_{O'}(\beta,\gamma)d\gamma}{\int_{-\gamma_m}^{\gamma_m} P_{O'}(\beta,\gamma)d\gamma} - \frac{\int_{-\gamma_m}^{\gamma_m} \gamma P_O(\beta,\gamma)d\gamma}{\int_{-\gamma_m}^{\gamma_m} P_O(\beta,\gamma)d\gamma} \quad (7)$$

and $$\frac{D}{D'} \approx \frac{L'}{L} \quad (8)$$

where L and L' are the angle width of the nonzero area of $P_O(\beta,\gamma)$ and $P_{O'}(\beta,\gamma)$, as shown in FIG. 13.

Figure 14:
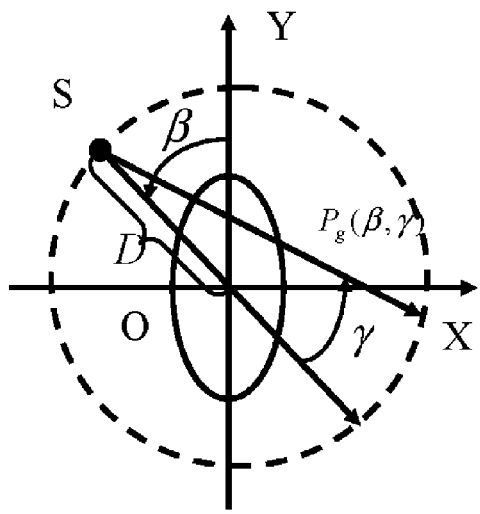
FIG. 14 represents an exemplary 360° reference scan.
Figure 15:
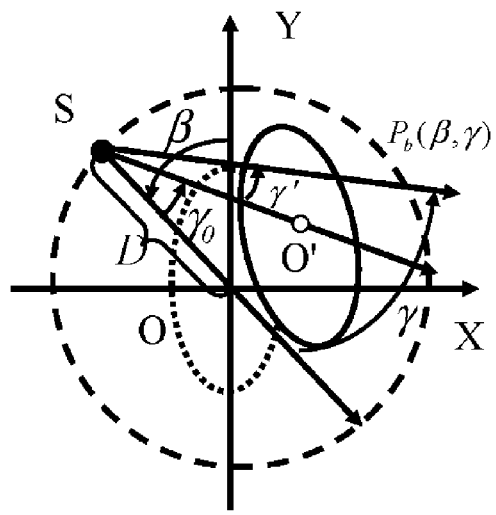
FIG. 15 represents an exemplary 360° bad scan.
Figure 16:
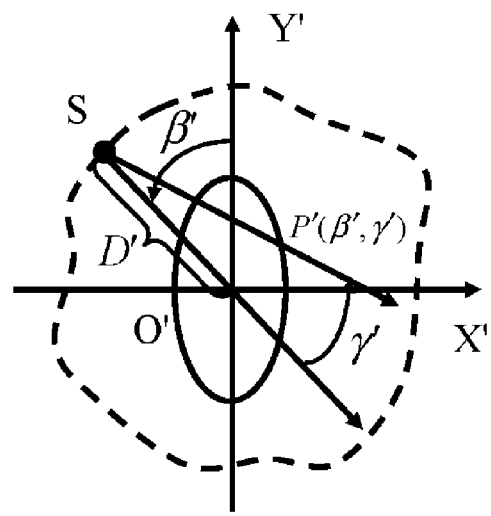
FIG. 16 represents an exemplary projection dataset to reconstruct an image in an exemplary head system.

Exemplary details for exemplary motion estimation based on correlation coefficient are presented herein. FIG. 14 represents an exemplary 360° reference scan. FIG. 15 represents an exemplary 360° bad scan. FIG. 16 represents an exemplary projection dataset to reconstruct an image in an exemplary head system.

In FIG. 14, the gravity center of the object is located at the origin, and during a 360° reference scan the projection dataset reported by the CT system is $\{P_g(\beta_i,\gamma_j)\}$ where view angle $$\beta_i = i\frac{2\pi}{N},$$

view number i=0,1, . . . , N−1, and the $\gamma_j$ is the discrete ray angle, ray number j=0,1, . . . , J−1. In FIG. 15, the object motion exists, and during the bad 360° scan the projection dataset reported by the CT system is $\{P_b(\beta_i,\gamma_j)\}$. To reconstruct the image in the head system in FIG. 16 in an example one employs a projection dataset in the head system $\{P'(\beta_i',\gamma_j')\}$ as well as the parameters $D_i'$, the distance between x ray source and the gravity center of the object. This is equivalent to find the geometric parameters $\beta_i',\gamma_0(i)$, and $D_i'$ for every bad projection $P_b(\beta_i,\gamma)$.

Exemplary steps follow with exemplary details presented herein. Step 1. Find the view angle $\beta_i'$ in the head system. Step 2, Calculate the $\gamma_0(i)$. Step 3, Calculate the D'(i).

Step 1. Find the view angle $\beta_i'$ in the head system. Based on the reference and bad projection datasets $\{P_g(\beta_i,\gamma_j)\}$, and $\{P_b(\beta_i,\gamma_j)\}$, one may define two N×J matrices $P_g(i,j')$ and $P_g(i,j')$ with i=0,1, . . . , N−1 and j=0,1, . . . , J−1 by the following interpolation equations, $$P_g(i,j')=P_g(\beta_i,\gamma_{is}+(\gamma_{il}-\gamma_{is})j'/J),$$

$$P_b(i,j')=P_b(\beta_i,\gamma_{is}+(\gamma_{il}-\gamma_{is})j'/J),$$

where $\gamma_{is}$ and $\gamma_{il}$ is the smallest and largest ray angle of every projection P $(\beta_i,\gamma_j)$ which can be a reference projection or a bad projection.

One may calculate the following exemplary correlation coefficients:

$$r_{ik} = \frac{\sum_{j'=0}^{J-1} P_b(i,j')P_g(i+k,j')}{\left(\sum_{j'=0}^{J-1} P_b^2(i,j') \sum_{j'=0}^{J-1} P_g^2(i+k,j')\right)^{\frac{1}{2}}}.$$

Here if the index i+k≧M, the index i+k is considered as i+k−M.

For every i, find the max of $\{r_{ik}\}_{k=0,1,N-1}$. Denoting the index of the max value is k=k(i), the view angle in head system for the i-th bad projection $P_b(\beta_i,\gamma_j)$ is $$\beta'(i) = k(i)\frac{2\pi}{N}.$$

Figure 17:
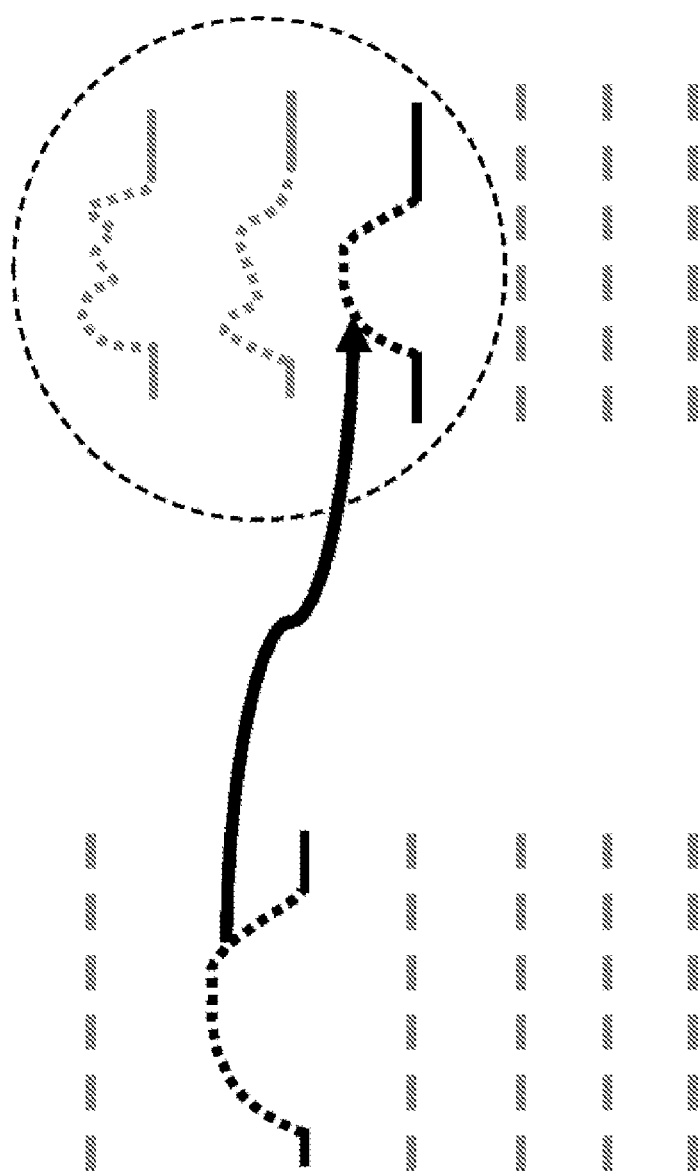
FIG. 17 represents exemplary correlation for projection angle in which an exemplary projection from an exemplary bad scan is matched with an exemplary projection in an exemplary reference scan.

One may find a most similar one in the reference projection dataset for every bad projection. FIG. 17 represents exemplary correlation for projection angle in which an exemplary projection from an exemplary bad scan is matched with an exemplary projection in an exemplary reference scan.

Step 2. Calculate the $\gamma_0(i)$.

Refer to FIGS. 13 and 15. Based on equation (7), the ray angle where the gravity center locates in an example is given by:

$$\gamma_0(i) = \frac{\int \gamma P_b(\beta_i, \gamma)d\gamma}{\int P_b(\beta_i, \gamma)d\gamma} - \frac{\int \gamma P_g(\beta_{k(i)}, \gamma)d\gamma}{\int P_g(\beta_{k(i)}, \gamma)d\gamma}.$$

Step 3, Calculate the D'(i).

Refer to FIG. 13. Based on the equation (8), the distance between the object center and the source in an example can be calculated from exemplary equation (9):

$$D(i) = \frac{L_{k(i)}}{L_i}D. \quad (9)$$

where $L_i, L_{k(i)}$ are the widths (or the lengths of support) of the projections $P_b(\beta_i,\gamma)$ and $P_g(\beta_{k(i)},\gamma)$, or the number of the non-zero elements of $P_b(\beta_i,\gamma_j)$ and $P_g(\beta_{k(i)},\gamma_j)$.

Finally, for every bad projection $P_b(\beta_i,\gamma)$ one may obtain the associate projection in head system $$P_b(\beta_i, \gamma) = P'\left(k(i)\frac{2\pi}{N}, \gamma - \gamma_0(i)\right),$$

and the associated distance between the source and gravity center of the object D'(i) is given by exemplary equation (9). This completes exemplary motion estimation of moderate motion.

Figure 18:
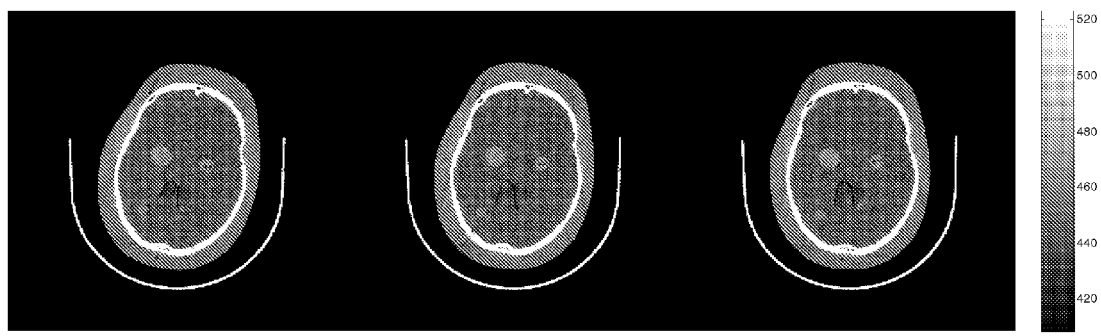
FIG. 18 represents exemplary direct reconstruction images of three exemplary 360° scans for an exemplary same physical phantom.

FIG. 18 represents exemplary direct reconstruction images of three exemplary 360° scans for an exemplary same physical phantom. FIG. 18 shows a physical phantom experiment. One may make a 360° scan for each of three poses of the phantom. Their images have serious mis-registration in FIG. 18.

Figure 19:
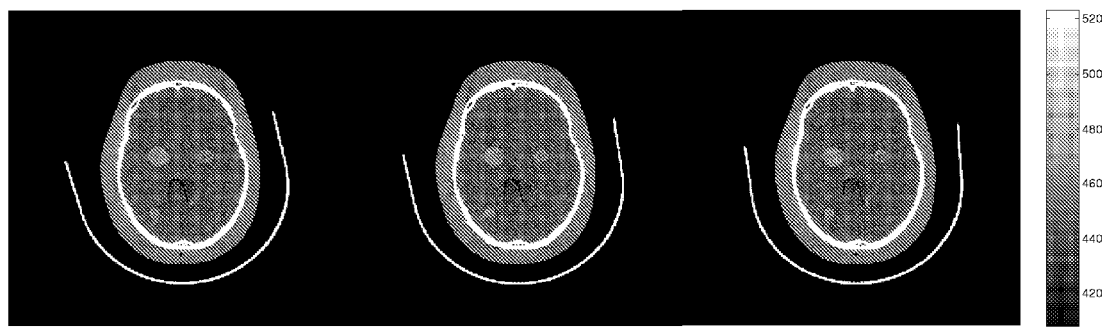
FIG. 19 represents exemplary corrected reconstruction for images by exemplary motion compensation.

One may connect the three 360° scan projection data and consider the formed dataset as a perfusion process with some sudden motion. One may apply an exemplary similar projection approach and obtain the exemplary resultant images of FIG. 19. The images now have a common pose. FIG. 19 represents exemplary corrected reconstruction for images by exemplary motion compensation.

Exemplary details for exemplary small motion estimation are presented herein. Rebinning may be employed. Even if the patient head is fixed well inside the holder with the attachment (FIG. 8), it is possible in an example that the minor unconscious motion still exists. In an example it is straightforward to find from the difference image of two reconstruct images. Such a small motion does not produce motion artifacts but result in mis-registration of the images. For small motion, one may rebin the fan-beam projection to parallel beam projection. The position difference between the bad scan and reference scan can be found from the two rebinned projection. Target reconstruction can be used.

Suppose one has a reference scan and a bad scan. An exemplary difference of the reference scan and bad scan is that they have a relatively small and/or little different gravity center and direction. Rebinning in an example serves to find their difference of position and directions. Exemplary rebinning in an example comprises a number of steps.

Step 1. Rebinning the reference and bad fan beam projection data $\{P_g(\beta_i,\gamma_j)\}$ and $\{P_b(\beta_i,\gamma_j)\}$ to obtain the parallel beam projection dataset $\{P_g(\theta_i,t)\}$ and $\{P_b(\theta_i,t)\}$ where the view angle $0 \le \theta_i < 180°$ and t is the distance of an x-ray to the origin. i=0,1,2, ... M−1 is the view index.

Step 2. Suppose the gravity center of the object is located at (x, y), which can be calculated by the projection at $\theta_i=0,\pi/2$ in exemplary equation (10):

$$x = \frac{\int tp(0, t)dt}{\int p(0, t)dt}, \quad y = \frac{\int tp(\frac{\pi}{2}, t)dt}{\int p(\frac{\pi}{2}, t)dt} \quad (10)$$

Based on this relation to calculate the object gravity center of the reference scan and the bad scan $(x_g, y_g)$ and $(x_b, y_b)$.

Step 3. Form two new datasets $\{P'_g(\theta_i,t)\}$ and $\{P'_b(\theta_i,t)\}$ by shifting the reference and bad parallel projection in exemplary equation (11):

$$p_g'(t,\theta) = p_g(t-(x_g \cos\theta + y_g \cos\theta),\theta)$$

$$p_b'(t,\theta) = p_b(t-(x_b \cos\theta + y_b \cos\theta),\theta) \quad (11)$$

Step 4. Resample the variable t of the reference and bad dataset $\{P'_g(\theta,t)\}$ and $\{P'_b(\theta,t)\}$ to form their discrete forms $\{P'_g(\theta_i,t_j)\}$ and $\{P'_b(\theta_i,t_j)\}$. Calculate their correlation coefficients in exemplary equation (12):

$$r(k) = \frac{\sum_{i,j} P'_g(\theta_i, t_j)P'_b(\theta_{i+k}, t_j)}{\left(\sum_{i,j} P'^2_g(\theta_i, t_j)\sum_{i,j} P'^2_b(\theta_{i+k}, t_j)\right)^{\frac{1}{2}}} \quad (12)$$

When the index in the above formula i+k≧M, the index is considered as i+k−M. Find the max of $\{r(k)\}_{k=0,1,...M-1}$. Denote the index of the max is $k_0$, then the object in the bad scan has a counterclockwise rotation along its center relative to the object in the reference scan in exemplary equation (13):

$$\alpha = k\frac{\pi}{M}. \quad (13)$$

To increase the accurate of the k value, one can estimated the max index k as a real number rather than integer according the change tendency near the max value, for example, parabola fitting.

Figure 20:
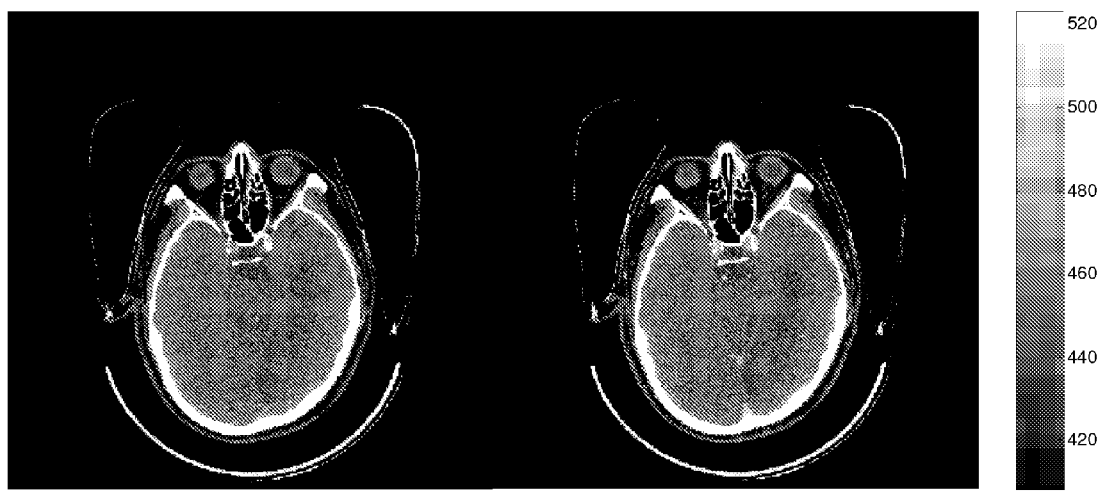
FIG. 20 represents exemplary first and fiftieth images of a patient from an exemplary perfusion study.
Figure 21:
FIG. 21 represents an exemplary image difference with and without exemplary motion compensation.

FIG. 20 represents exemplary first and fiftieth images of a patient from an exemplary perfusion study. FIG. 21 represents an exemplary image difference with and without exemplary motion compensation. Exemplary minor motion exists between the first and fiftieth images in FIG. 20. Applying exemplary rebinning, one may find their small difference of position. Utilizing this position information, compensated images have a reduced difference, as shown in FIG. 21.

Exemplary implementations follow. An imaging system in an example comprises an x-ray source, a detector, a data acquisition system (DAS), and a computer. The x-ray source emits a beam of x-rays toward an object to be imaged. The detector receives x-rays emitted by the x-ray source. The DAS is operably connected to the detector. The computer is operably connected to the DAS and programmed to estimate motion of the object on a correlation-basis and through employment of earlier-collected data.

The computer operably connected to the DAS in an example is programmed to correlate among data obtained in a plurality of scans of the object to correct data from a subset of the plurality of scans based on an estimation of the motion of the object. The computer operably connected to the DAS in an example is programmed to employ a reference scan projection dataset of the object as the earlier-collected data; interpret the reference scan projection dataset as being acquired in a coordinate system associated with the object; and find a most similar one in the reference projection dataset for every bad projection aided by an exact or approximate geometrical and physical imaging process model.

The computer operably connected to the DAS in an example is programmed to handle translation and rotation of the object in estimation of the motion of the object on the correlation-basis and through employment of the earlier-collected data. The computer operably connected to the DAS in an example is programmed to decompose in-plane motion of the object into a plurality of basic motions having a clear effect on projection data.

The computer operably connected to the DAS in an example is programmed to employ a reference scan projection dataset of the object as the earlier-collected data.

The computer operably connected to the DAS in an example is programmed to interpret as a reference scan of the object a good scan that comprises substantially little and/or substantially no motion of the object in estimation of the motion of the object. The computer operably connected to the DAS in an example is programmed to employ a reference scan of the object as the earlier-collected data and a reference for other scans of the object in estimation of the motion of the object.

The computer operably connected to the DAS in an example is programmed to correlate between data in different scans to correct bad scan data in estimation of the motion of the object. In an example, the object comprises a head and the computer operably connected to the DAS is programmed to interpret as a reference scan of the object a scan that comprises substantial stillness of the head; and employ the reference scan as the earlier-collected data and a reference for other scans of the head in estimation of the motion of the head. The computer operably connected to the DAS in an example is programmed to interpret the motion of the head as substantially rigid motion inside a scanning plane.

The x-ray source in an example emits the beam of x-rays toward the object in a fan-beam geometry. The x-ray source in an example emits the beam of x-rays toward the object in a cone-beam geometry. The imaging system in an example comprises an MR system.

A medical computed tomography (CT) system in an example comprises an x-ray source, a detector, a data acquisition system (DAS), and a computer. The x-ray source emits a beam of x-rays toward a head to be imaged. The detector receives x-rays emitted by the x-ray source. The DAS is operably connected to the detector. The computer is operably connected to the DAS and programmed to estimate the motion of the head during head perfusion based on correlation of data collected earlier during the head perfusion.

The computer operably connected to the DAS in an example is programmed to correlate among data obtained in a plurality of scans of the head to correct data from a subset of the plurality of scans in estimation of the motion of the head.

In an example, a beam of x-rays is emitted toward an object to be imaged. Motion of the object is estimated on a correlation-basis and through employment of earlier-collected data.

In an example, a reference scan is reconstructed to obtain an image of the object, and an actual position of the object is determined through reduction of error between simulated projection and measured projections. In an example, a projection is found in a reference scan that comprises a similar profile for a projection in a bad scan to obtain an approximate similar relation of projection profiles, and motion parameters are estimated for reconstruction based on the approximate similar relation of projection profiles. In an example, fan-beam projection data is rebinned to parallel beam projection data, and a position difference between a bad scan and a reference scan is determined from the parallel beam projection data.

The steps or operations described herein are examples. There may be variations to these steps or operations without departing from the spirit of the invention. For example, the steps may be performed in a differing order, or steps may be added, deleted, or modified.

The present invention has been described in terms of the preferred embodiment, and it is recognized that equivalents, alternatives, and modifications, aside from those expressly stated, are possible and within the scope of the appending claims.

What is claimed is:

1. An imaging system, comprising:
   an x-ray source that emits a beam of x-rays toward an object to be imaged;
   a detector that receives x-rays emitted by the x-ray source;
   a data acquisition system (DAS) operably connected to the detector; and
   a computer operably connected to the DAS and programmed to:
   calculate object location parameters from a first object scan;
   calculate object location parameters from a second object scan;
   correlate the object location parameters from the first and second object scans;
   estimate an amount of object motion that occurred during the second object scan based on the correlation;
   correct projection data in the second object scan based on the estimate; and
   generate an image of the object from the second object scan using the corrected projection data of the second scan.

2. The imaging system of claim 1, wherein the computer operably connected to the DAS is programmed to:
   identify the first object scan as a reference dataset wherein the object remained motionless.

3. The imaging system of claim 2, wherein the computer operably connected to the DAS is programmed to:

interpret the reference dataset as being acquired in a reference coordinate system associated with the object; and
determine a reference origin of the object.

4. The imaging system of claim 3, wherein the computer operably connected to the DAS is programmed to:
determine translation and rotation motion of the object within the reference coordinate system.

5. The imaging system of claim 2, wherein the computer operably connected to the DAS is programmed to:
determine the object location parameters with respect to a reference origin determined from the reference dataset.

6. The imaging system of claim 1, wherein the computer operably connected to the DAS is programmed to:
determine an actual position of the object during the second object scan using the corrected projection data in the second object scan.

7. The imaging system of claim 1, wherein the computer operably connected to the DAS is programmed to:
interpret as a reference scan of the object a good scan that comprises substantially little and/or substantially no motion of the object in estimation of the motion of the object.

8. The imaging system of claim 1, wherein the computer operably connected to the DAS is programmed to:
employ a reference scan for other scans of the object in estimation of the motion of the object.

9. The imaging system of claim 1, wherein the computer operably connected to the DAS is programmed to:
correlate between data in different scans to correct scan data in estimation of the motion of the object.

10. The imaging system of claim 1, wherein the object comprises a head, wherein the computer operably connected to the DAS is programmed to:
interpret as a reference scan of the object a scan that comprises substantial stillness of the head; and
employ the reference scan as a reference for other scans of the head in estimation of the motion of the head.

11. The imaging system of claim 10, wherein the computer operably connected to the DAS is programmed to:
interpret the motion of the head as substantially rigid motion inside a scanning plane.

12. The imaging system of claim 1, wherein the x-ray source emits the beam of x-rays toward the object in a fan-beam geometry.

13. The imaging system of claim 1, wherein the x-ray source emits the beam of x-rays toward the object in a cone-beam geometry.

14. The imaging system of claim 1, wherein the imaging system further comprises an MR system.

15. A medical computed tomography (CT) system, comprising:
an x-ray source that emits a beam of x-rays toward a head to be imaged;
a detector that receives x-rays emitted by the x-ray source;
a data acquisition system (DAS) operably connected to the detector; and
a computer operably connected to the DAS and programmed to:
acquire a plurality of scans of a head during head perfusion, each scan comprising a plurality of projections;
identify at least one of the plurality of scans as a reference scan;
characterize motion of the head in non-reference scans of the plurality of scans as one of large, moderate, and small, based on the identified reference scan, the motion of the head occurring during acquisition of the non-reference scans; and
correct the plurality of projections of at least one non-reference scan of the plurality of scans based on the characterization.

16. The medical CT system of claim 15, wherein the computer operably connected to the DAS is programmed to:
correlate among data obtained in the plurality of scans of the head to correct data from a subset of the plurality of scans in estimation of the motion of the head.

17. A method, comprising the steps of:
obtaining an average object position from a plurality of object scans;
defining a first projection data set of the object as a reference scan based on a first position of the object obtained from the first projection data set and a correlation of the first position with the average object position;
determining a shape and an orientation of the object from the reference scan;
obtaining a second projection data set from the object;
determining a shape and an orientation of the object from the second projection data set;
estimating motion of the object based on a correlation of the respective shapes and orientations of the object between the reference scan and the second projection data set;
correcting at least one projection of the second projection data set based on the estimation; and
generating an image of the object using the corrected projection data set.

18. The method of claim 17, wherein the step of estimating comprises the steps of:
reconstructing the reference scan to obtain an image of the object; and
determining an actual position of the object through reduction of error between simulated projections and measured projections.

19. The method of claim 17, wherein the step of estimating comprises the steps of:
identifying a projection in the reference scan as having a profile that is similar to a profile in a projection in another scan; and
estimating motion parameters for reconstruction based on the relation of projection similar profiles.

20. The method of claim 17, wherein the step of estimating comprises the steps of:
rebinning fan-beam projection data to parallel beam projection data; and
determining a position difference between one scan and the reference scan from the parallel beam projection data.

* * * * *